United States Patent [19]

Kosaka

[11] Patent Number: 4,477,434

[45] Date of Patent: Oct. 16, 1984

[54] MEDICINAL COMPOSITIONS, FOODS AND BEVERAGES HAVING THERAPEUTIC EFFECTS ON DISEASES OF CIRCULATORY SYSTEM AND DIGESTIVE SYSTEM

[76] Inventor: Reiko Kosaka, 3/27, Hannan-cho 6-chome, Abeno-ku, Osaka-shi, Osaka-fu, Japan

[21] Appl. No.: 497,029

[22] Filed: May 23, 1983

[30] Foreign Application Priority Data

May 29, 1982 [JP] Japan ................................ 57-91794
Jul. 15, 1982 [JP] Japan ................................ 57-124237

[51] Int. Cl.$^3$ ............................................. A61K 37/48
[52] U.S. Cl. ...................................................... 424/94

[58] Field of Search ........................................... 424/94

[56] References Cited

U.S. PATENT DOCUMENTS 3,939,260  2/1976  Lafon .................................. 424/28

Primary Examiner—Stanley J. Friedman
Attorney, Agent, or Firm—Murray, Whisenhunt and Ferguson

[57] ABSTRACT

Medicinal compositions, foods and beverages having therapeutic effects on diseases of the circulatory system and the digestive system and characterized by papain and citric acid contained therein.

11 Claims, No Drawings

MEDICINAL COMPOSITIONS, FOODS AND BEVERAGES HAVING THERAPEUTIC EFFECTS ON DISEASES OF CIRCULATORY SYSTEM AND DIGESTIVE SYSTEM

The present invention relates to medicinal compositions, foods and beverages having therapeutic effects on diseases of the circulatory system and the digestive system.

Diseases of the circulatory system include diabetes which involves accumulation of glucose in the blood and excretion of glucose into the urine, kidney diseases which are caused by the disorder of blood filtration function permitting excretion of protein into the urine, hemorrhoids which cause swelling and pain in the anus, hypertension which results from increased resistance in peripheral blood vessels or production of hypertensive substances, gout which is thought attributable to increases and variations in blood uric acid value, etc. These diseases have close relation to functional disorders of the circulatory system.

Hypertrophy of the liver, hepatitis, pancreatitis, etc. can be said to be diseases of the digestive system.

Effective drugs have yet to be developed for the treatment of these diseases of the circulatory and digestive systems. Therapies presently resorted to are alimentotherapy, symptomatic treatment with use of insulin, administration of adrenocortical hormones, installation of an artificial kidney, surgical removal of piles, etc.

Citric acid, which is thought effective on diabetes, kidney diseases, etc., has found limited use, but the effect is insufficient and takes time for appearance. Further because the acid is difficult to administer, the patient usually discontinues the administration of the acid during treatment.

In view of the above situation, I have conducted intensive research on drugs useful for diabetes and like diseases of the circulatory system and hepatitis and like diseases of the digestive system and found that the conjoint use of citric acid and papain, a kind of enzyme, surprisingly produces a remarkable effect very rapidly for the treatment of various diseases of the circulatory system and the digestive system.

For example, when I who had hypertension, administered a mixture of papain and citric acid, the blood pressure dropped to a normal level in a short period of time with disappearance of headaches. Accordingly the drug was given to many people suffering from diseases of the circulatory system, such as diabetes, kidney disease and hypertension, or diseases of the digestive system, such as hepatitis and pancreatitis, for tens of years to find the surprising result that the excretion of glucose into the urine ceased in as short a period as about 4 days to 1 week after the start of the administration, with decreased swelling in the legs and a drop of the blood pressure to a normal level.

The mixture of citric acid and papain, in which the unique acid taste of citric acid is mitigated, is much easier to take than citric acid alone. I have further found that the mixture as admixed with foods or beverages can be taken very naturally almost without becoming conscious of the presence of the mixture as a drug.

The present invention provides medicinal compositions, foods and beverages having therapeutic effects on diseases of the circulatory system and the digestive system and characterized by papain and citric acid contained therein.

The medicinal compositions, foods and beverages of the present invention are effective for treating diseases of the circulatory system, such as diabetes, kidney diseases, hemorrhoids, hypertension, heart diseases, gout, stiffness of the shoulder, constipation, asthma and skin diseases, and diseases of the digestive system, such as hypertrophy of the liver, hepatitis and pancreatitis.

The medicinal composition of the invention is much easier to take than when citric acid is taken singly and exhibits its effect in an extremely short period of time. The therapeutic effect is so remarkable that even patients given up by doctors can be cured. The food and beverage of the present invention exhibit a therapeutic effect also in a very short period of time when ingested and have the advantage of being much easier to take than citric acid alone and the mixture of citric acid and papain which is prepared merely in the form of particles, tablets or an aqueous solution. The medicinal composition, food and beverage of the invention have another advantage in that the preparation, when taken, eliminates the body odor and oral odor from man and animals and the unique odor of their excretions. For example, when given to a dog or cat, the preparation eliminates the smell thereof and the odor of its excretion.

The papain to be used in this invention is the enzyme collected from the fruit of papaya. It is advantageously used usually in the form of particles or granules. The citric acid to be used is usually one commercially available.

The medicinal composition of the invention can be in the form of various preparations including, for example, particles, tablets, pellets, granules, aqueous solutions, capsules, suspensions, syrups, etc. for oral administration, and injections, suppositories, etc. for non-oral administration. Known carriers are usable as excipients for such preparations. Also usable are other additives, such as filler, binder, lubricant, wetting agent, etc. It is especially advantageous to administer the medicinal composition of the invention in the form of particles or an aqueous solution.

The food and beverage of the present invention can be in a wide variety of forms, such as juice, aerated drink, milk, alkaline drink or like ion-containing drink, milk powder, coffee, tea, cocoa, cola, honey, yogurt, jelly, ice cream, soybean milk, Japanese tea, miso soup, Japanese noodle, Chinese noodle, frizzled rice, sushi, additives for cooking, etc., which are not limitative.

It is also useful to add vitamin C and other vitamins to the medicinal composition, food and beverage of the present invention.

While the proportions of papain and citric acid which are the effective component compounds to be contained in the medicinal composition, foods and beverages of the invention can be in a wide range, it is preferable to use 0.05 to 20 parts by weight, more preferably 0.5 to 5 parts by weight, of the latter per part by weight of the former.

Although the combined amount of the effective components of the medicinal composition of the invention is not particularly limited but can be in a wide range, it is usually about 1 to about 100% by weight, preferably about 20 to about 100% by weight, based on the whole composition.

The combined amount of the effective components of the food or beverage is not particularly limited either but can be in a wide range. However, it is usually about 0.5 to 20% by weight, preferably about 5 to about 10% by weight, based on the whole food or beverage.

The amount of the composition, food or beverage of the invention to be ingested, which is determined suitably according to the method of ingestion, age of the patient, degree of the disease, etc., is usually about 50 mg to about 10 g per day in terms of the combined amount of the effective components. It is desirable to daily take such an amount once or up to about 10 times in divided portions.

Medicinal compositions, foods and beverages of the present invention will be described with reference to the following preparation examples and clinical examples showing pharmacological effects.

PREPARATION EXAMPLE 1

Papain (50 mg) and 50 mg of citric acid were mixed together to obtain a medicinal composition (powder) of the invention.

PREPARATION EXAMPLE 2

Papain (50 mg), 100 mg of citric acid and 200 mg of starch were mixed together to obtain a medicinal composition (powder) of the invention.

PREPARATION EXAMPLE 3

Papain (50 mg) and 150 mg of citric acid were dissolved in 100 ml of water to obtain a medicinal composition (aqueous solution) of the invention.

PREPARATION EXAMPLE 4

Papain (100 mg) and 50 mg of citric acid were dissolved in 100 ml of water to obtain a medicinal composition (aqueous solution) of the invention.

1. Therapeutic effects on diabetes (1) Patient K. I., 60-year-old male

His father and two uncles also had diabetes. At the age of about 30 and ever since, glucose was frequently found excreted into the urine, with a blood glucose level of about 160. Despite the treatment received from the doctor, the symptoms remained for tens of years without improvements. Around April 1982, he started administration of the composition of the invention twice daily in the morning and evening. In about 4 days, glucose totally disappeared from the urine. Even when checked 2 hours after taking sweet food, the urine was no longer found to contain glucose. With the composition given for about one month up to date, he is now free from stiffness in the shoulders, recovered from hemorrhoid and feels comfortable every day.

(2) Patient K. S., 49-year-old male

Since he was about 30 years old, large excesses of glucose were detected in the urine with continued symptoms of diabetes. Although suffering also from gastric ulcer, he was unable to receive surgery. While administering insulin for years, he started administration of the present composition three times daily around May 1981. On the 4th day of the administration, glucose disappeared from the urine, with the blood sugar value recovered to a normal level. The patient thereafter successfully undertook surgery for gastric ulcer. Presently he is in good health free from stiffness in the shoulders.

(3) Patient K. M., 57-year-old female

In 1979 she was found to have a high blood sugar value and was told by the doctor not to take any sweet food. However, she received no drug therapy, and diabetes remained uncured. When she started administering the present composition three times a day in June 1979, glucose disappeared on the 4th day, and the blood sugar value recovered to a normal level in one month. Presently she is in good health free from stiffness in the shoulders.

2. Therapeutic effects on kidney diseases (1) Patient K. M., 65-year-old male

Since July 1973, edema in the legs became apparent with anemic symptoms, and he was hospitalized on July 17, 1973 also with the symptoms of gout. He was discharged in November 1973 without complete cure and was thereafter treated as an outpatient with a drug of adrenocortical hormone, but the symptoms remained unchanged. In June 1979, he started administering the present composition three times daily, with disappearance of urine protein on the 10th day. In 3 months thereafter, he discontinued administration of the adrenocortical hormone drug conjointly given with the composition. He is now in good health free from stiffness in the shoulders.

(2) Patient H. I., 70-year-old male

He was hospitalized in 1977 due to kidney disease. He was treated with a drug of adrenocortical hormone but discharged in one month without improvement. When he started administering the present composition three times daily in June 1981, swelling disappeared from the legs on the 4th day with normal excretion of the urine, and he restored his health.

(3) Patient K. T., 50-year-old female

In 1970 she developed a kidney disease with continual edema in the body in the morning and evening. When she began to administer the present composition twice daily in May 1979, the edema disappeared on the 4th day. She is now in good health with a comfortable body condition.

3. Therapeutic effects on hypertension (1) Patient T. T., 60-year-old male

He had hypertension for 30 years, with a maximum blood pressure rising to 200 or 250 at a time, and was given hypotensive drugs for these years. When he began to administer the present composition three times daily in August 1979, the blood pressure recovered to a normal level on around 10th day, which was surprising even to the doctor. He is now in good health.

(2) Patient K. S., 50-year-old male

Due to hypertension with a maximum blood pressure of 170, he started to administer the present composition once or twice daily in June 1981. In one week, the blood pressure returned to a normal level, and stiffness disappeared from the shoulders.

(3) Patient K. S., 52-year-old female

She had hypertension with a blood pressure of 160/125. Intravenous infusion given resulted in no reduction in the blood pressure. When she began to administer the present composition three times daily in June 1981, a normal blood pressure was restored in 2 weeks, with disappearance of stiffness from the shoulders.

(4) Patient R. K., 50-year-old female

She had hypertension with a maximum blood pressure of 170, a weak heart and frequent headaches but administered no hypotensive drug. When she started administering the present composition twice daily in May 1979, the blood pressure returned to a normal level in 2 weeks with disappearance of headaches and stiffness from the shoulders.

PREPARATION EXAMPLE 5

With 180 ml of cow's milk were admixed 3 g of papain, 5 g of citric acid and 5 g of sugar, and the mixture was thoroughly stirred to obtain a beverage of the invention.

PREPARATION EXAMPLE 6

With 100 g of yogurt were admixed 2 g of papain and 5 g of citric acid, and the mixture was thoroughly stirred to obtain a beverage of the invention.

PREPARATION EXAMPLE 7

With 100 ml of soybean milk were admixed 5 g of papain and 10 g of citric acid, and the mixture was thoroughly stirred to obtain a beverage of the invention.

PREPARATION EXAMPLE 8

With 200 ml of a juice were admixed 3 g of papain, 2 g of citric acid and 100 mg of vitamin C, and the mixture was thoroughly stirred to obtain a beverage of the invention. Therapeutic effects (1) Patient H. K., 60-year-old male The patient, suffering from a heart disease for years, had a heart attack in April 1980 and was hospitalized. He thereafter left the hospital but felt depressed and heavy in his legs as unique symptoms of heart diseases. When he began to drink cow's milk prepared according to the invention twice to three times daily in May 1982, the heaviness of the legs disappeared in about one month.

(2) Patient Z. N., 57-year-old male

He had 2/3 of one of this lungs removed by surgery in the past. Although it was not apparent whether this was the cause, he suffered seriously from stiffness of the shoulders for years. Daily moxibustion with use of as much as a handful of moxa and administration of various drugs including one containing chlorella proved ineffective. When he started drinking a beverage of the invention prepared from cow's milk and honey three times daily in April 1982, the stiffness disappeared from the shoulders in about 20 days to one month.

(3) Patient K. M., 57-year-old female

Twenty years ago, she had eczema on the instep, which became itchy and sored red when wet. Drugs for dermatophytosis and commercial ointment of adrenocortical hormone, although applied, failed to cure the disease. She took pellets of the present composition three times daily at a dose of about 10 pellets each time as admixed with cooked rice, tea, water or the like. The disease was cured completely in about one month.

(4) Patient S. Y., 26-year-old female

At the age of 15 and ever since, she had eczema and rash over the entire body with red spots. The symptoms remained unchanged for about 11 years despite the administration of various drugs. When she started administering a beverage and food of the invention three times daily at a dose of about 30 pellets each time in February 1983, the spots became thinner in about two weeks, with improvements in the symptoms.

(5) Patient S. N, 50-year-old female

She was hospitalized for 4 months in 1965 due to acute hepatitis and jaundice. In 1975, she developed cystitis due to the side effects of drugs and was hospitalized again for one month.

She was hospitalized for 3 months in 1980 due to the aggravation of the liver disease. The symptoms thereafter improved considerably with the administration of herb medicines. However, she became very tired and had a full stomach about three times a month.

When she started ingesting a beverage and food prepared according to the invention three times daily at a dose of about 10 pellets each time in March 1983, she became comfortable in about 20 days with clean urine and disappearance of fullness of the stomach, constipation and stiffness of the shoulders.

I claim:

1. A composition comprising 0.5-20% by weight, based on the total composition, of an admixture of papain and citric acid; and 99.5-80% by weight, based on the total composition, of an ingredient selected from the group consisting of food, beverage or mixture thereof.

2. The composition as claimed in claim 1, wherein said composition comprises 5-10% by weight, based on the total composition, of said admixture of papain and citric acid; and 95-90% by weight, based on the total composition, of said ingredient.

3. The composition as claimed in claim 1, wherein said citric acid is present in said admixture in an amount of 0.05-20 parts by weight per part by weight of papain.

4. The composition as claimed in claim 3, wherein said citric acid is present in said admixture in an amount of 0.5-5 parts by weight per part by weight of papain.

5. A composition comprising 1-100% by weight, based on the total composition, of an admixture of papain and citric acid and 0-99% by weight, based on the total composition, of a pharmaceutically acceptable excipient in the form of particles, tablets, pellets, granules or solutions.

6. The composition as claimed in claim 5, wherein said composition is in the form of a solution.

7. The composition as claimed in claim 6, wherein said solution is an injectable solution.

8. The composition as claimed in claim 6, wherein said solution is an aqueous solution.

9. The composition as claimed in claim 5, wherein said citric acid is present in said admixture in an amount of 0.05-20 parts by weight per part by weight of papain.

10. The composition as claimed in claim 9, wherein said citric acid is present in said admixture in an amount of 0.5-5 parts by weight of papain.

11. The composition as claimed in claim 5, wherein said composition comprises 20-100% by weight, based on the total composition, of said admixture of citric acid and papain; and 0-80% by weight, based on the total composition, of said pharmaceutically acceptable excipient.

* * * * *